United States Patent [19]

Geistlich et al.

[11] Patent Number: 5,573,771
[45] Date of Patent: Nov. 12, 1996

[54] MEDICINAL BONE MINERAL PRODUCTS

[75] Inventors: Peter Geistlich, Stansstad; Rolf W. Pfirrmann, Lucerne, both of Switzerland

[73] Assignee: Osteomedical Limited, Dublin, Ireland

[21] Appl. No.: 391,247

[22] Filed: Feb. 21, 1995

Related U.S. Application Data

[63] Continuation of Ser. No. 258,361, Jun. 10, 1994, abandoned, which is a continuation of Ser. No. 115,792, Sep. 3, 1993, abandoned, which is a continuation of Ser. No. 876,114, Apr. 29, 1992, abandoned, which is a continuation of Ser. No. 469,609, Jun. 19, 1990, abandoned.

[30]     Foreign Application Priority Data

Aug. 19, 1988 [GB]  United Kingdom ............... 8819755

[51] Int. Cl.⁶ ........................ A61F 13/00; A61K 9/16
[52] U.S. Cl. ................. 424/422; 424/423; 424/426; 424/489; 424/490; 424/41; 424/492; 424/44; 623/11; 623/16; 623/66
[58] Field of Search ................... 424/422, 423, 424/426, 484, 549, 489–492, 494; 623/16, 66; 530/356; 514/2, 8, 21

[56]            References Cited

U.S. PATENT DOCUMENTS

| | | | |
|---|---|---|---|
| 2,968,593 | 1/1961 | Rapkin | 167/74 |
| 4,314,380 | 2/1982 | Miyata et al. | 3/1.9 |
| 4,347,234 | 8/1982 | Wahlig et al. | 424/15 |
| 4,434,094 | 2/1984 | Seyedin et al. | 260/112 R |
| 4,455,256 | 6/1984 | Urist | 260/112 R |
| 4,587,268 | 5/1986 | Pfirrmann | 514/774 |
| 4,629,464 | 12/1986 | Takata et al. | 623/16 |
| 4,654,464 | 3/1987 | Mittelmeier | 623/16 |
| 4,888,366 | 12/1989 | Chu et al. | 523/115 |

FOREIGN PATENT DOCUMENTS

| | | |
|---|---|---|
| 0147021 | 7/1985 | European Pat. Off. |
| 182483 | 5/1986 | European Pat. Off. |
| 182483 | 5/1986 | European Pat. Off. |
| 0197693 | 10/1986 | European Pat. Off. |
| 0243178 | 10/1987 | European Pat. Off. |
| 8901347 | 2/1989 | Germany. |
| 0058041 | 4/1983 | Japan. |
| 0058041 | 4/1983 | Japan. |
| 3125258 | 5/1988 | Japan ............... 623/16 |
| 8607266 | 12/1986 | WIPO. |
| 8607265 | 12/1986 | WIPO. |

OTHER PUBLICATIONS

Lange review of Medical Physiology. 1987 p. 323.
Losee et al., "Bone treated with Ethylenediamine as a Successful Foundation Material in Cross–Species Bone Grafts", *Nature* vol. 177, Jun. 1956.
Solomons, T., *Organic Chemistry*, 2nd Ed. John Wiley & Sons, (1980) P. 808.
Skinner et al., "Preparation of the Mineral Phase of Bone Using Ethylenediamine Extractin", *Calc. Tiss. Res.*, 10, (1972) pp. 257–268.
Kershaw, R., "Preparation of Anorganic Bone Grafting Material", *The Pharmaceutical Journal*, 8 (1963) p.537.
Williams, et al., "Preparation of the Inorganic Matrix of Bone", *Science*, vol. 119 (1954) pp. 771–773.
Stegmann et al., "Uber die anorganische Knochensubstanz nach Formamidaufschluss", Bd. 320 (1960) 272.
Hurley, et al., "Anorganic Bone—Chemistry, Anatomy, and Biological Reactions", *Military Medicine* (1957), pp. 101–104.
*Merck Index*, entry 4276, p. 685, 1990.
*Merck Index*, entry 1701, p. 256, 1990.

*Primary Examiner*—Gollamudi S. Kishore
*Attorney, Agent, or Firm*—Rothwell, Figg, Ernst & Kurz

[57]             ABSTRACT

The invention provides a purified particulate bone mineral product for use in medicine, the particles of said mineral being substantially free from all endogenous organic material and having at least at the surface thereof resorbable, physiologically compatible, natural or synthetic macromolecular material. In particular the invention provides a bone mineral impregnated with a gel-forming protein or polysaccharide such as gelatin to provide a surprising increase in strength and a product comprising bone mineral in a matrix of collagen-fibres and a gel-forming protein. Such products are intended as remodeling implants or prosthetic bone replacement.

8 Claims, No Drawings

MEDICINAL BONE MINERAL PRODUCTS

This is a continuation of application Ser. No. 08/258,361, filed Jun. 10, 1994, now abandoned, which is a continuation of application Ser. No. 08/115,792, filed Sep. 3, 1993, now abandoned, which is a continuation of application Ser. No. 07/876,114, filed on Apr. 29, 1992, now abandoned, which is a continuation of application Ser. No. 07/469,609, filed as PCT/GB89/01020, Aug. 16, 1989, published as WO90/01955, Mar. 8, 1990.

This invention relates to improvements in bone mineral products of large specific surface area.

Bones from slaughtered animals are an inexpensive raw material available in large quantities. They contain 50 to 60% of very finely crystallized hydroxylapatite bonded by collagenic tissue and containing significant qualities of proteinaceous and other matter as well as associated fat and muscle tissues. In view of its biologically formed crystal structure it can also be considered as a highly biocompatible prosthetic bone replacement. Owing to its large specific surface it can also be used, for example, as an adsorbent or as a support for slow release medication.

Natural bone mineral comprises hydroxyapatite-like crystallites with a particular degree of crystallinity, habit and size (irregular plate-like morphology, 5–10nm in thickness 10–50 nm in length) and surface chemistry resulting from the calcium to phosphate ratio (37.5–38.0% calcium and 15.5–5–19.0% phosphorus). Also present in the natural bone mineral are small amounts of noncrystalline entities and other calcium phosphate crystalline phase including the minerals Brushite and Whitlockite, and octa-calcium phosphate. The inorganic phase of bone contains porosity including ultrastructural interstices (10–100 nm) between the crystallities occuring naturally and produced by removal of the organic phase, and microscopic spaces (1–20 microns) including osteocyte lacunae, canaliculi, vascular channels, volkman's canals, and the canals of haversian systems (100–500 nm). The specific surface area, which is a measure of porosity is in the range 50 to 100 $m^2/gm$ as determined by mercury porosimetry. The crystallinity of bone mineral can be characterized by X-ray diffraction and the porosity and crystallite morphology and size by electron microscopy. Small amounts of nonapatitic crystallites can be detected by thermogravimetric analysis.

We have found however, that the composition and structure of natural bone mineral cannot be duplicated by products formed in vitro or by naturally occurring hydroxyapatites prepared previously. Two methods for the purification of natural bone mineral have been proposed namely calcination and solvent extraction.

The temperature needed during calcination for the incineration of the organic constituents of the bones are rather high. This leads to extensive recrystallization of the mineral part with formation of much coarser crystals. The so formed material exhibits a relatively small specific surface. Thus, such material is not readily remodelled to form new bone on implantation and implants may remain unremodelled indefinitely although this may be acceptable for some purposes.

In the extraction processes the proteins are extracted from degreased bone with a suitable solvent. The resulting bone mineral is then washed to remove the solvent.

In both cases, when organic impurities are removed from the natural bone to leave only the bone mineral, the strength of the material is greatly reduced and the individual pieces of purified bone mineral are consequently extremely brittle. This renders handling of the material difficult and may lead to undesirable effects on implantation. We have found, however, that adequate strength can be imparted to the brittle bone mineral by providing, at least on the surface, a macromolecular substance such as gelatin or collagen which is non-antigenic and which is resorbable on implantation.

According to the present invention we provide a purified particulate bone mineral product for use in medicine, the particles of said mineral being substantially free from all endogenous organic material and having at least at the surface thereof resorbable, physiologically compatible, natural or synthetic macromolecular material.

The macromolecular material may impregnate each of the individual particles to improve the handling properties of the product in manufacture and use. In that case, the weight ratio of the macromolecular material to the purified bone mineral is advantageously greater than 1:10, preferably greater than 1:8 and less than 4:1, preferably less than 1:2. The macromolecular material penetrates the porous structure of the bone mineral and effectively replaces some of the natural proteinaceous material previously present in natural bone which, although providing strength, also gives immunological tissue reactions on implantation of the bone mineral.

The macromolecular material may be a protein such as gelatin or collagen, which may be cross-linked to give additional strength and freedom from antigencity. Thus, for example, gelatin preferably bone gelatin, may be cross-linked with 0.2 to 2% by weight e.g. about 0.6% formaldehyde. Other cross-linking agents include other aldehydes such as glyoxal and glutaraldehyde and bifunctional molecules such as diisocynates, e.g. hexamethylene diisocyanate, diepoxides and peroxides. The cross-linking agent should be fully reacted so as not to remain as such in the material.

The macromolecular material may also be a polysaccharide such as dextran or agarose or a synthetic polymer such as lactic polyester.

The macromolecular material may also be used to provide a matrix for the particulate bone mineral from which shaped articles may be formed. In this case, it is particularly preferred to use a fibrous macromolecular substance such as a fibrous collagen particularly Type I or Type I-III, together with a gel forming macromolecular substance such as gelatin. The weight ratio of the fibrous material to the bone mineral may, for example, be in the range 1:20 to 3:20 e.g. about 1:10. The gel phase advantageously amounts to 2 to 8% by weight of the bone mineral, e.g. about 5%. Where gelatin is used as the gel phase, it may be lightly cross-linked, e.g. with about 0.2% formaldehyde.

We have found that bone mineral treated in accordance with the invention, in particular with fibrous protein such as collagen, is far less subject to the problem of particle migration than uncoated bone mineral particles.

The bone mineral product according to the invention may be used as a remodelling implant or prosthetic bone replacement, for example in orthopoedic surgery, including hip revisions, replacement of bone loss, e.g. in traumatology, remodelling in maxillo-facial surgery or filling periodontal defects and tooth extraction sockets, including ridge augmentation. The impregnated particulate material of the invention may thus be used for packing into a variety of bone cavities and its reduced brittleness is significant in aiding the handling and packing procedure.

The fibre matrix embodiment of the invention lends itself to the preparation of moulded shapes for bone remodelling. The dry matrix material, usually in the form of sheets, may be cut to approximate size, moistened to soften the matrix material and moulded the desired shape.

The purified bone mineral may, for example, be a product as described in International Patent Application WO 86/07265 (PCT/GB86/00310). Such products may be prepared by rigorously de-greasing particulate bone, e.g. bovine femurs, and treating with ammonia or an organic amine to degrade residual protein followed by extensive water washing. Such material remains resorbable on implementation assisting the remodelling process.

It has also be proposed to prepare purified bone mineral by calcinating particulate cancellous or cortical bone e.g. at 900° C. for 24 hours. Such calcined bone mineral is of use where permanent, non-resorbable implants are required, for example in ridge augmentation. In either way after removal of organic material, the bone is excessively brittle and its strength is greatly improved by treatment according to the invention.

Where the bone is to be used as a drug carrier, as indicated in the above International Patent Application the bone mineral may usefully carry one or more absorbed drugs or other physiologically active substances.

Physiologically active substances which may be adsorbed onto the bone mineral are preferably at least partially water-soluble and include anti-bacterial substances such as antibiotics, e.g. penicillins, cephalosporins, aminoglycosides etc., sulphonamides and, in particular, condensation products of formaldehyde with taurinamide or N-substituted taurinamide. The latter compounds may be represented by the formula

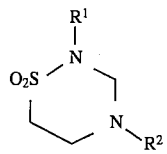

where $R^1$ is hydrogen or a $C_{1-4}$ alkyl group and $R^2$ is hydrogen or a group of the formula

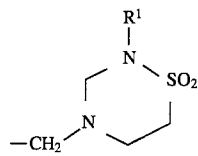

wherein $R^1$ has the above meaning.

The compound of formula (I) in which $R^1$ and $R^2$ are both hydrogen is taurultam while the compound in which $R^1$ is hydrogen and $R^2$ has the formula (II) is taurolidine. These compounds act as methylol transfer agents and are effective not only in destroying both gram negative and gram positive bacteria but also in inactivating both endotoxins and exotoxins produced by the bacteria.

Other useful physiologically active substances include proteins and polypeptides capable of assisting bone regeneration especially non-collagenous proteins derived from bone matrix and bone cells. These include mitogenic factors such as skeletal growth factor and morphogenic and angiogenic factors as well as transforming bone growth factor. Growth factors from the natural bone matrix such as ossein or more preferably osteopoietin are particularly beneficial.

It will be appreciated that physiologically active substances may alternatively or additionally be incorporated in the macromolecular substance e.g. impregnated gelatin. This is particularly suitable for proteins such as the bone growth factors set out above.

The bone mineral will normally be in the form of particles of average diameter in the range 0.1 to 10 mm. Pieces of cancellous bone will commonly be in the upper size range, e.g. 2 to 10 mm in diameter, and may provide shaped inserts; such cancellous bone is particularly brittle due to the large size of the pores therein and benefits very greatly from treatment according to the invention. Particles for incorporation into collagen fibre will commonly be of cortical bone and will generally be in the size range 0.1 to 3 mm, preferably 0.25 to 2 mm. It may be beneficial to the close packing of the bone mineral particles to use a mixture of two or more particle sizes, e.g. 0.25 to 1 mm and 1 to 2 mm or a broad range e.g. 0.25 to 2 mm.

The purified bone mineral may be obtained, for example, by the method described in the above International Patent Application. Thus, for example, fats may be removed using one or more conventional fat solvents such as ethers, e.g. diethyl ether; ketones e.g. acetone; or hydrocarbons or halogenated hydrocarbons e.g. heptane or methylcylcohexane or toluene.

It may be advantageous to remove an extractant such as toluene by an intermediate extraction with a water miscible solvent such as ethanol before proceeding further. Collagen material may be dissolved using proteolytic agents such as bases e.g. potassium hydroxide in glycerol, or organic bases such as amines, e.g. ethylene diamine, or amides such as formamide, preferably at elevated temperatures. Such agents are preferably water-miscible to facilitate removal by water washing. Especially good results have been obtained using bone extracted with refluxing ethylene diamine.

Extraction may advantageously be continued at each stage, if necessary with changes of solvent, until no further material is extracted, e.g. for periods up to one or two weeks. It may be advantageous to comminute further after initial protein removal since the bone is more readily fractured at that stage than before extraction. After treatment with base, excess solvents are rigorously removed e.g. by evaporation and/or, where suitable, water washing. Water washing may for example be effected for long periods at 100° C. to ensure that all the solvent and dissolved substances are removed.

The material is normally subjected to a drying step. It may be convenient to sterilise the material at this stage, e.g. by heat treatment which may effect further purification. Absorption and/or adsorption of the physiologically active substance is preferably effected by immersing the treated bone mineral in an aqueous solution thereof preferably under sterile conditions. The concentration of the active substance is preferably relatively high to facilitate adsorption and/or absorption and will depend in part on the solubility of the active material.

The following Examples are given by way of illustration only:

PREPARATION

Bovine femur bones were boiled in hot water until clean, comminuted to a particle size of 5 to 10 mm. and extracted under reflux with toluene for 24 hours in a Sohxlet apparatus. The material was further extracted with ethanol to remove toluene and then extracted at elevated temperature with an azeotropic mixture of ethylene diamine and water 85:15) for 8 days, with several changes of solvent until substantially no further organic material was extracted. After extraction the material was washed with hot water at 100° C. for 10–14 days with frequent changes of water. The product was then air dried at 100° C.

The dried product was further comminuted to an average particle size of 0.2 to 2 mm and sterilized in the autoclave.

Pieces of bovine femur spongeosa bone, typical diameter 10 mm, were purified by the same technique, omitting the final granulation.

EXAMPLE 1

45.0 g gelatin (food grade, No.8 mesh, 280 g.Bloom) were dissolved in 452 g distilled water at 60° C. 3.0 g of 35% w/w aqueous formaldehyde were added to this solution. While this solution was still warm, 100 g of deproteinated spongeosa (cancellous) bone in relatively large pieces purified as above were added and a vacuum applied and then released. Such evacuation/release cycles were repeated five times. Then the mixture was left to stand at room temperature for seven days and the bone pieces were then separated from the gel and dried in vacuo at 60° C. The treated bone pieces were packed in polyethylene containers and sterilised by gamma irradiation.

The results are given in the following Table

| Material | Ball pressure hardness | Compressive strength |
| --- | --- | --- |
| 1) Degreased cancellous bone | 6.4 N/mm$^2$ | 8.0 N/mm$^2$ |
| 2) Deproteinated degreased cancellous bone (1) | 2.5 N/mm$^2$ | 0.8 N/mm$^2$ |
| 3) Deproteinated cancellous bone (2), gelatin coated | 5.1 N/mm$^2$ | 4.0 N/mm$^2$ |

EXAMPLE 2

2.0 g of collagen fibre felt were comminuted with 500 g, distilled water in a blender. This dispersion was centrifuged and the supernatant water removed. To the resulting collagen fibre slurry were added 17.5 g of granulated cortical bovine bone purified by the above procedure, followed by thorough mixing and removal of water by suction (70 mm). The granulated bone had a particle size 0.5 to 1.0 mm. After removal of water 5 mls of a 9% w/w aqueous gelatin solution were added (cross-linked with 0.6% of 35% aqueous formaldehyde) and the mixture again suction dried.

The sponge mass was cut into pieces and dried in vacuo at 60° C. The pieces of sponge were packed into polyethylene containers and sterilised by gamma irradiation.

EXAMPLE 3

The procedure described in Example 1 is repeated, but instead of formaldehyde, 3 g of 30% w/w of glyoxal are used.

EXAMPLE 4

Pieces of deproteinated, degreased bone, 1 to 2 cm in size, are immersed in a 1% w/w solution of medical collagen. Vacuum is applied and released consecutively 5 times. After soaking for one week at room temperature the bone pieces are drained and then dried at 60° C. under vacuum. The material is packed in polystyrene containers and sterilised by irradiation with 25 kGy gamma radiation.

EXAMPLE 5

Example 4 is repeated with 1% collagen solution to which 2 g of 35% w/w formaldehyde solution per litre have been added.

In a further example the formaldehyde solution has been replaced by the same amount of an aqueous 30% w/w glyoxal solution.

We claimed:

1. A particulate bone mineral product for use in medicine comprising porous bone mineral particles derived from natural bone having a crystal structure of natural bone and substantially free from all endogenous organic material, the particles having an average diameter in the range of 0.1 to 10 mm, and having at least at the surface thereof resorbable, physiologically compatible, collagen fibers in an amount which increases the strength of the bone mineral particles wherein the weight ratio of said collagen fibers to said porous bone mineral particles is at least 1:20'.

2. A product as claimed in claim 1 in which the bone mineral is prepared by completely de-greasing particulate bone and treating it with ammonia or an amine to degrade residual protein followed by extensive water washing.

3. A product as claimed in claim 1 which further comprises at least one absorbed pharmaceutically active substance.

4. A product as claimed in claim 3 in which said pharmaceutically active substance is taurolidine or taurultam.

5. A product as claimed in claim 3 in which said physiologically active substance is capable of assisting bone regeneration and is selected from morphogenic growth factors, angiogenic growth factors, transforming growth factors, ossein, and osteopoietin.

6. A method of treatment of a human or animal subject wherein a bone mineral product as claimed in claim 1 is used as a remodelling implant or prosthesis.

7. A product as claimed in claim 1 in which the weight ratio of the collagen fibers to the bone material is in the range of 1:20 to 3:20.

8. A product as claimed in claim 1, further comprising gelatin in a gel phase, wherein said collagen fibers are present in said gel phase, and wherein said gel phase comprises 2 to 8% by weight of the bone material.

* * * * *